United States Patent [19]
Nobuyoshi et al.

[11] Patent Number: 5,397,306
[45] Date of Patent: Mar. 14, 1995

[54] CATHETER

[75] Inventors: Masakiyo Nobuyoshi, Kitakyusyu; Kyuta Sagae, Nakai, both of Japan

[73] Assignee: Terumo Kabushiki Kaisha, Tokyo, Japan

[21] Appl. No.: 157,391

[22] Filed: Nov. 23, 1993

Related U.S. Application Data

[60] Division of Ser. No. 989,925, Dec. 11, 1992, abandoned, which is a continuation of Ser. No. 629,593, Dec. 18, 1990, abandoned.

[30] Foreign Application Priority Data

Dec. 20, 1989 [JP] Japan .................. 1-330198

[51] Int. Cl.$^6$ .................. A61M 29/00; A61M 25/00
[52] U.S. Cl. .................. 604/96; 604/280; 606/194
[58] Field of Search .................. 604/96–103, 604/265, 282; 606/192–194

[56] References Cited

U.S. PATENT DOCUMENTS

| | | | |
|---|---|---|---|
| 3,566,874 | 3/1971 | Shepherd et al. | 604/265 |
| 3,736,939 | 6/1973 | Taylor | 604/265 |
| 3,861,396 | 1/1975 | Vaillancourt et al. | 604/265 |
| 3,913,565 | 10/1975 | Kawahara | 128/2 M |
| 3,983,879 | 10/1976 | Todd | 604/96 |
| 4,411,655 | 10/1983 | Schreck | 604/287 |
| 4,459,318 | 7/1984 | Hyans | 604/265 X |
| 4,723,936 | 2/1988 | Buchbinder et al. | 604/95 |
| 4,762,129 | 8/1988 | Bonzel | 604/96 |
| 4,776,844 | 10/1988 | Ueda | 604/281 |
| 4,884,557 | 12/1989 | Takehana et al. | 604/281 |
| 4,884,573 | 12/1989 | Wijay et al. | 604/96 |
| 4,925,445 | 5/1990 | Sakamoto et al. | 604/95 |
| 4,998,923 | 3/1991 | Samson et al. | 604/96 |
| 5,019,040 | 5/1991 | Itaoka et al. | 604/281 |
| 5,025,799 | 6/1991 | Wilson | 604/96 |
| 5,055,101 | 10/1991 | McCoy | 128/657 |
| 5,156,594 | 10/1992 | Keith | 604/96 |
| 5,279,560 | 1/1994 | Morrill et al. | 604/96 |

*Primary Examiner*—C. Fred Rosenbaum
*Assistant Examiner*—Frank Wilkens III
*Attorney, Agent, or Firm*—Frishauf, Holtz, Goodman & Woodward

[57] ABSTRACT

The catheter of the present invention comprises a body portion, a distal portion and an internal lumen and at least the above body portion includes a super-elastic metallic tube. This catheter has a high efficiency of transmitting the pushing force given at its proximal end (pushability) and a high torque transmission efficiency. Furthermore, since the body portion of the catheter includes a super-elastic metallic tube, the wall thickness of the body portion can be made sufficiently thin and a catheter with a smaller diameter can be formed.

21 Claims, 4 Drawing Sheets

CATHETER

This application is a division of application Ser. No. 07/989,925, filed Dec. 11, 1992, abandoned, which is a continuation of application Ser. No. 07/629,593, filed Dec. 18, 1990, (abandoned).

BACKGROUND OF THE INVENTION

This invention relates to a catheter, for example, a catheter to be inserted into a blood vessel such as a catheter for angiography or a catheter for dilating a blood vessel.

A catheter for angiography to be inserted into a blood vessel consisting of a main body formed of a somewhat soft thermoplastic resin and a rigidity imparting member consisting of a metallic braided wire (generally a stainless-steel wire) and disposed around the main body which is for inhibiting kinking or squash of the catheter while maintaining its high flexibility and for improving the torque transmission efficiency has conventionally been designed.

A catheter equipped with an inflatable member for dilating a stenosis portion in a blood vessel to improve the blood flow on the peripheral side of the stenosis portion which is for use in curing the stenosis portion is disclosed in EPA No. 349640 for example. This catheter comprises an inner tube made of a flexible synthetic resin, an outer tube made of a flexible synthetic resin and disposed coaxially with the inner tube and a foldable and inflatable member having a proximal end portion attached to the outer tube and a distal portion attached to the inner tube, and besides, the inner or outer tube is provided with a rigidity imparting member consisting of a metallic wire (e.g., a stainless-steel wire).

The rigidity imparting member used in the above catheter can inhibit its kinking or squash and improve its torque transmission efficiency to some extent. However, the catheter as a whole had low rigidity and particularly had a low efficiency of transmitting the pushing force given at its proximal end (pushability) and only an insufficient torque transmission efficiency.

Catheters are required to be introduced into peripheral blood vessels year by year, catheters which can be introduced into a more peripheral blood vessel has come to be desired.

However, the above catheter, whose body portion consists of a synthetic resin tube, needs to have a certain wall thickness and therefore necessarily has a large outer diameter. Accordingly, the blood vessel into which the catheter can be introduced is restricted by its outer diameter and the catheter could only be introduced into a blood vessel sufficiently larger than the outer diameter of the catheter.

SUMMARY OF THE INVENTION

The object of the present invention is to provide a novel and improved catheter of the design that has a high efficiency of transmitting the pushing force given at its proximal end (pushability) and a high torque transmission efficiency and furthermore can be made to have a sufficiently thin wall thickness and a smaller diameter.

According to the present invention, there is provided a catheter comprising a body portion, a distal portion and an internal lumen and at least the body portion includes a super-elastic metallic tube.

According to the present invention, there is provided a catheter equipped with an inflating member which comprises a body portion which forms an internal lumen and includes a super-elastic metallic tube having openings in a distal portion; a guide portion for guiding the catheter which is attached to distal portion of said body portion; and a deflatable or foldable inflating member which has a tip portion attached to the guide portion or the distal portion of the above body portion and a rear end portion attached to the body portion and communicates with the lumen through the above openings.

According to the present invention, there is provided a catheter comprising an inner tube which has a body portion, a distal portion and a first lumen whose tip is open; an outer tube which is disposed coaxially with said inner tube, has a body portion, a distal portion and a distal tip recessed by a predetermined distance from a distal tip of the inner tube and forming a second lumen between an inner surface of said outer tube, and an outer surface of said inner tube; a deflatable or foldable and inflatable member which has a tip portion attached to the inner tube and a rear end portion attached to the outer tube and communicates with the second lumen near said rear end portion; a first opening disposed at the proximal portion of said inner tube and communicating with the first lumen; and a second opening disposed at the proximal portion of the outer tube and communicating with the second lumen, wherein at least one of the body portions of the inner and outer tubes includes a super-elastic metallic tube.

DETAILED DESCRIPTION OF THE PREFERRED EMBODIMENTS

Figure 1:
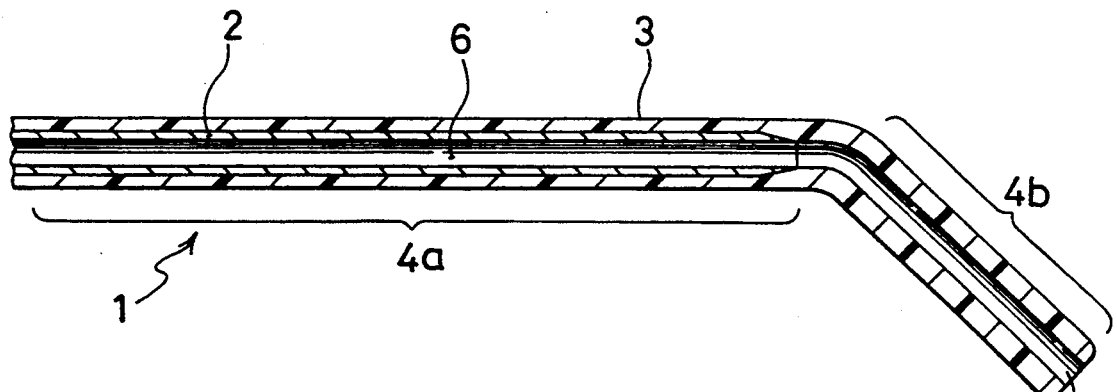
FIG. 1 is a partial longitudinal cross section of a catheter according to one preferred embodiment of the present invention.

The catheter of the present invention will be described according to examples shown in the drawings.

The catheter generally designated at 1 according to the present invention comprises a body portion 4a, a distal portion 4b and an internal lumen 6 and at least the body portion 4a includes a super-elastic metallic tube 2.

Therefore, the catheter of the present invention has a high efficiency of transmitting the pushing force given at its proximal end (pushability) and a high torque transmission efficiency and can be made to have a sufficiently thin wall thickness and a smaller diameter.

A catheter according to one preferred embodiment of the present invention shown in FIG. 1 and FIG. 10 will be described in the following.

The catheter 1 of this preferred embodiment is an example wherein the catheter of the present invention is applied to a catheter for angiography and comprises a body portion 4a, a distal portion 4b, a lumen 6 continuous from the proximal end of the catheter 1 to its distal end, a tip end opening 5 and a hub 7 fixed to the proximal end.

The body portion 4a comprises a super-elastic metallic tube 2 and a synthetic resin tube 3 covering the outer surface of the super-elastic metallic tube 2, and the synthetic resin tube 3 protrudes from the distal portion of the super-elastic metallic tube 2 to form the distal portion 4b of the catheter.

The super-elastic metallic tube 2 is preferably formed of super-elastic alloys, for example, Ti-Ni alloys containing 49~58 atom % of Ni, Cu-Zn alloys containing 38.5~41.5% by weight of Zn, Cu-Zn-X alloys containing 1~10% by weight of X wherein X is selected from the group consisting of Be, Si, Sn, Al and Ga and Ni-Al alloys containing 36~38 atom % of Al. The most preferred alloys are Ti-Ni alloys of the above composition. The super-elastic metallic tube 2 preferably has an outer diameter of 0.3~6.0 mm, more preferably 0.4~5.5 mm and a wall thickness of 40~200 μm, more preferably 50~150 μm. It preferably has a length of 500~4,000 mm, more preferably 800~3,000 mm, a buckling strength (yield stress under load) of 5~200 kg/mm$^2$ at 22° C., more preferably 8~180 kg/mm$^2$ at 22° C., and a restoring stress (yield stress upon unloading) of 3~180 kg/mm$^2$ at 22° C., more preferably 5~160 kg/mm$^2$ at 2220 C. It is preferable that the tip of the super-elastic metallic tube 2 be tapered as shown in FIG. 1 in order to prevent the tip from being separated from the synthetic resin tube 3. It is not necessary that the super-elastic metallic tube have the above outer diameter over its entire length and it is allowed to make its part to have the above outer diameter.

As shown in FIG. 1, it is preferable that the synthetic resin tube 3 cover the entirety of the super-elastic metallic tube 2 and protrude from the distal portion of the super-elastic metallic tube 2 to form the distal portion 4b of the curved catheter. This enables the catheter 1 of this example to have a flexible distal portion 4b. The curved portion has a shape suitable for the predetermined blood vessel into which the catheter is to be inserted.

For the synthetic resin tube 3, thermoplastic resins such as polyolefin elastomer (e.g., polyethylene elastomer, polypropylene elastomer and ethylene-propylene copolymer elastomer), polyvinyl chloride, ethylene-vinyl acetate copolymer, polyamide elastomer, polyurethane and fluorine resin and silicone rubber can be used. It is preferred to use polyamide elastomer or polyurethane. It is preferable that the synthetic resin tube 3 be sufficiently flexible to allow free kinking of the super-elastic metallic tube 2. In addition, it is preferred to incorporate a radiopaque substance into the synthetic resin to form the tube 3 because it becomes more easy to locate the catheter 1 during its introduction into the blood vessel. The radiographically sensitive substance may be a metal such as Ba, W, Bi or a compound thereof in fine powdery form. The synthetic resin tube 3 has preferably an outer diameter of the 0.9~7.0 mm, more preferably 1.0~6.0 mm and a wall thickness on the outer surface of the super-elastic metallic tube 2 of 0.04~0.3 mm, more preferably 0.06~0.2 mm.

The outer surface of the synthetic resin tube 3 may be coated with a biocompatible especially antithrombotic resin such as polyhydroxyethyl methacrylate, or hydroxyethyl methacrylate-styrene copolymer (e.g., a HEMA-St-HEMA block copolymer). Particularly, when a material containing a radiopaque substance is used for the synthetic resin tube 3, it is preferred to perform the above coating in order to remove the roughness of the outer surface due to the radiopaque substance. Although it is preferable that the resin be a biocompatible one, a thin coating of the material used to form the synthetic resin tube 3 is also allowed.

It is preferred to apply hydrophilic treatment to the outer surface of the synthetic resin tube 3 in order to make it exhibit lubricity when contacted with blood or the like. Such hydrophilic treatments include coating with hydrophilic polymer such as poly(2-hydroxyethyl methacrylate), polyhydroxyethyl acrylate, hydroxypropyl cellulose, methylvinyl ether-maleic anhydride copolymer, polyethylene glycol, polyacrylamide or polyvinyl pyrrolidone.

It is preferable that the tip of the catheter 1 (tip of the synthetic resin tube 3) have a curved surface such as a semi-spherical surface as shown in FIG. 1 in order to prevent any damage to the blood vessel wall and to improve the operability of the catheter 1.

Figure 10:
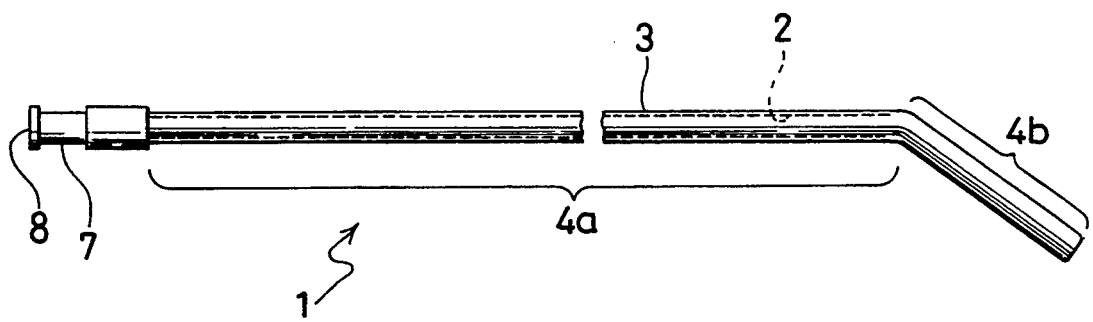
FIG. 10 is a view of a catheter according to another preferred embodiment of the present invention.

The hub is fixed to the proximal end of the body portion 4a shown in FIG. 10. The hub 7 has an opening 8 communicating with the lumen 6 and constituting an injection port for injecting X-ray contrast medium.

The hub 7 is preferably formed of thermoplastic resins, for example, polycarbonate, polyamide, polysulfine, polyallylate and methacrylate-butylene-styrene copolymer. Instead of providing such hub, an open end of the proximal end of the body portion may constitutes an injection port.

Figure 2:
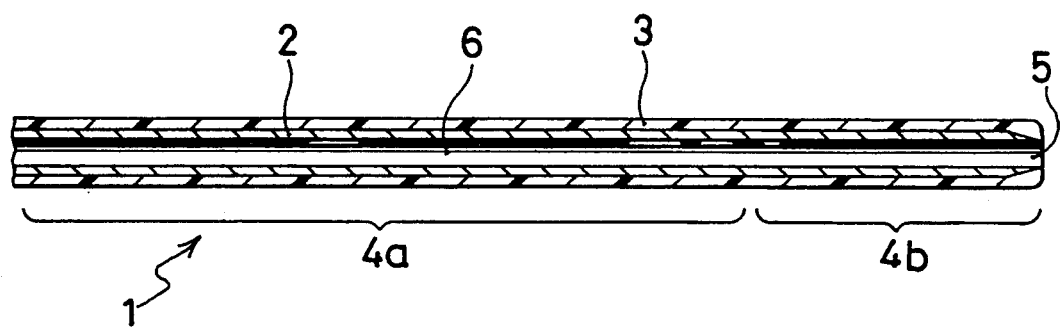
FIG. 2 is a partial longitudinal cross section of a catheter according to another preferred embodiment of the present invention.

Next, a catheter according to one preferred embodiment of the present invention shown in FIG. 2 will be described.

The catheter 1 of this preferred embodiment is an example wherein the catheter of the present invention is applied to a catheter for angiography. This catheter comprises a body portion 4a, a distal portion 4b, a lumen 6 continuous from the proximal end of the catheter 1 to its distal tip, a tip end opening 5 and a hub (not shown). The body portion 4a and the distal portion 4b consist of a super-elastic metallic tube 2 and a synthetic resin layer 3 covering the outer surface of the tube 2.

Those described above can suitably be used for the super-elastic metallic tube 2. It is preferable that the part of the tube 2 corresponding to the body portion 4a be highly rigid and the part of the tube 2 corresponding to the distal portion 4b be more flexible than another portion of tube 2. Such a super-elastic metallic tube can be formed by separately thermally treating the body portion of the super-elastic metallic tube 2 and its distal portion under different conditions so that the body portion has a large yield stress and the distal portion has a small yield stress and is elastic.

Figure 3:
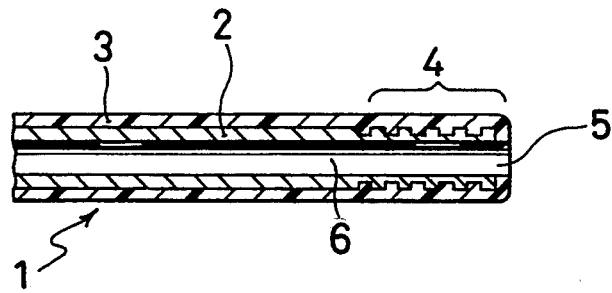
FIG. 3 is a partial longitudinal cross section of a catheter according to another preferred embodiment of the present invention.
Figure 4:
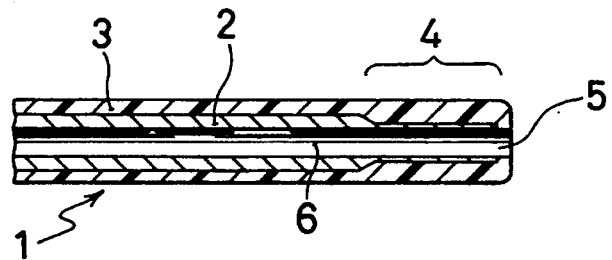
FIG. 4 is a partial longitudinal cross section of a catheter according to another preferred embodiment of the present invention.

As shown in FIG. 3, the outer surface of the distal portion of the super-elastic metallic tube 2 may be provided with annular grooves in order to make distal portion elastic. The groove is not restricted to annular one and it may be a spiral one. As shown in FIG. 4, the distal portion of the super-elastic metallic tube 2 may have a smaller diameter. As shown in FIG. 2, the synthetic resin layer 3 covers the entirety of the super-elastic metallic tube 2. For the synthetic resin layer 3, thermoplastic resins such as polyolefin (e.g., polyethylene, polypropylene and ethylene-propylene copolymer), polyvinyl chloride, ethylene-vinyl acetate copolymer, polyamide elastomer, polyurethane, fluorine resin and silicone rubber can be used. It is preferred to use a polyolefin, a polyamide elastomer or a polyurethane.

It is preferable that the synthetic resin layer 3 be sufficiently flexible to allow free kinking of the super-elastic metallic tube 2. In addition, it is preferred to incorporate a radiopaque substance into the synthetic resin to form the tube 3 because it becomes more easy to locate the catheter 1 during its introduction into the blood vessel. The radiographically sensitive substance may be a metal such as Ba, W, Bi or a compound thereof in fine powdery form.

The synthetic resin layer 1 preferably has an outer diameter of 0.9~7.0 mm, more preferably 1.0~6.0 mm and a wall thickness on the outer surface of the super-elastic metallic tube 2 of 0.04~0.3 mm, more preferably 0.06~0.2 mm. It is preferable that the tip of the catheter (tip of the synthetic resin tube 3) has a curved surface such as a semi-spherical surface in order to prevent any damage to the blood vessel wall and to improve the operability of the catheter 1. As mentioned above, the synthetic resin layer 3 may be coated with an antithrombotic resin and hydrophilic treatment may be applied to the outer surface of the layer 3 so as to make it exhibit lubricity.

The hub is similarly shown in FIG. 10 fixed to a proximal end of the body portion 4a. The hub has an opening communication with the lumen 6 and constituting an injection port for injecting X-ray contrast medium.

Figure 5:
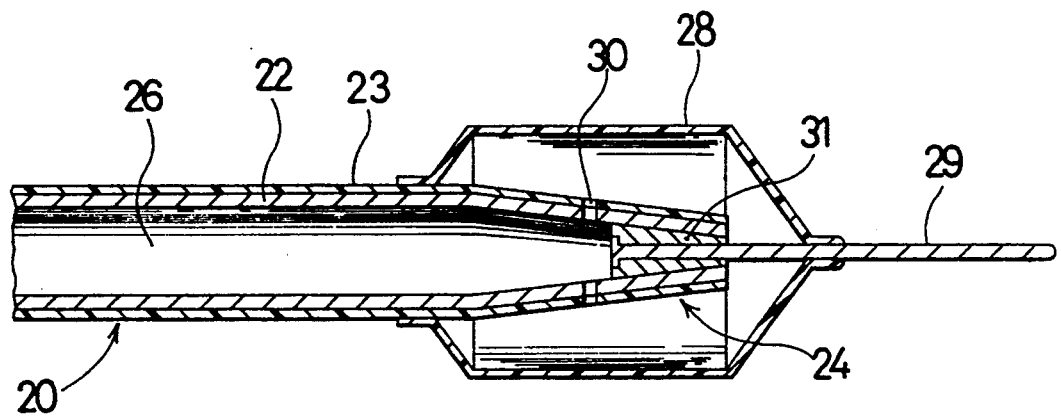
FIG. 5 is a partial longitudinal cross section of a catheter according to another preferred embodiment of the present invention.

Next, an example wherein the catheter of the present invention is applied to a catheter for dilating a blood vessel shown in FIG. 5 will described.

The catheter 20 comprises a body portion 24 which forms an internal lumen 26 and includes a super-elastic metallic tube 22 having openings 30 in its distal portion; a guide portion 29 for guiding the catheter fixed to the tip of the body portion 24; and a deflatable or foldable and inflatable member 28 having a rear distal portion attached to the guide portion 29 and a proximal end portion attached to the body portion 24 and which communicates with the lumen 26 through the perforation 30; and a hub (not shown) fixed the proximal end of the body portion 24.

The body portion 24 comprises the super-elastic metallic tube 22 and a synthetic resin layer 23 covering the outer surface of the tube 22. Although the synthetic resin layer 23 should not necessarily be provided, it is preferably provided in order to inhibit the adhesion of blood to the surface of the super-elastic metallic tube 22 and to facilitate the fixation of the inflatable member to be mentioned later.

The super-elastic metallic tube 22 is preferably formed of super-elastic alloys, for example, such as Ti-Ni alloys containing 49~58 atom % of Ni, Cu-Zn alloys containing 38.5~41.5% by weight of Zn, Cu-Zn-X alloys containing 1~10% by weight of X wherein X is selected from the group consisting of Be, Si, Sn, Al and Ga, or Ni-Al alloys containing 36~38 atom % of Al. The most preferred alloys are Ti-Ni alloys of the above composition. The super-elastic metallic tube 22 preferably has an outer diameter of 0.2~5 mm, more preferably 0.3~4 mm and a wall thickness of 50~200 $\mu$m, more preferably 80~150 $\mu$m. It preferably has a length of 500~4,000 mm, more preferably 1,000~3,000 mm, a buckling strength (yield stress under load) of 5~200 kg/mm$^2$ at 22° C., more preferably 8~150 kg/mm$^2$ at 22° C., and a restoring stress (yield stress upon unloading) of 3~180 kg/mm$^2$ at 22° C., more preferably 5~130 kg/mm$^2$ at 22° C.

It is preferable that the distal portion of the super-elastic metallic tube 22 be tapered as shown in FIG. 5. The distal portion of the super-elastic tube 22 is provided with perforation 30. The synthetic resin layer 23 covers the entirety of the super-elastic metallic tube 22 without closing the perforation 30. For the synthetic resin layer 23, thermoplastic resin such as polyolefin (e.g., polyethylenes, polypropylene, ethylene-propylene copolymer), polyvinyl chloride, ethylene-vinyl acetate copolymer, polymide elastomer and polyurethane, flourine resin and silicone rubber can be used. It is preferred to use polyolefin, polyamide elastomer or polyurethane.

It is preferable that the synthetic resin layer 23 be sufficiently elastic to allow free bending of the super-elastic metallic tube 22. The synthetic resin layer 23 preferably has a wall thickness of 5~300 $\mu$m, more preferably 10~200 $\mu$m.

The outer surface of the synthetic resin layer 23 may be coated with a biocompatible especially antithrombotic resin such as a polyhydroxyethyl methacrylate or hydroxyethyl methacrylate-styrene copolymer (e.g., HEMA-St-HEMA block copolymer).

In a catheter equipped with an inflatable member according to the present invention, it is preferred for facilitating the insertion into a blood vessel and further into a guide catheter to apply hydrophilic treatment to the outer surfaces of the body portion 24 and the inflatable member 28 which have the possibility of contacting with blood during use so as to make them exhibit lubricity when contacted with blood or the like.

Such hydrophilic treatments include coating with hydrophilic polymers such as poly (2-hydroxyethyl methacrylate), polyhydroxyethyl acrylate, hydroxypropyl cellulose, methylvinyl ether-maleic anhydride copolymer, polyethylene glycol, polyacrylamide or polyvinyl pyrrolidone.

The guide portion 29 is fixed to the distal tip of the body portion 24. It functions as a guide wire for guiding the catheter 1 to a predetermined site in a blood vessel. As the guide portion 29, a member prepared by winding a thin metallic wire around a super-elastic or elastic metallic wire preferably a super-elastic metallic wire can be used for example. The guide portion 29 preferably has an outer diameter of 0.2~1.0 mm and a length of about 2~150 mm. It preferably has a buckling strength (yield stress under load) of 5~200 kg/mm$^2$ at 22° C., more preferably 8~150 kg/mm$^2$ at 22° C., and a restoring stress (yield stress upon unloading) of 3~180 kg/mm$^2$ at 22° C., more preferably 5~150 kg/mm$^2$ at 22° C.

As shown in FIG. 5, the guide portion 29 has at its rear end portion provided a flange which is inserted into the tip of the body portion 44 and fixed to it by soldering. A scale wax such as silver solder or gold solder can suitably be used as the solder. The guide portion 29 may be fixed to the distal tip of the body portion by caulking the tip after inserting the rear end portion of the guide portion 29 into the tip.

The inflatable member 28 is deflatable or foldable and can be folded around the body portion 24 and the guide portion 29. At least a part of the inflatable member 28 is an almost circular cylinder with an almost equal diameter so that a structure portion in a blood vessel can easily be expanded and the inflatable member 28 is foldable. The above almost circular cylindrical part may not be a completely circular cylinder and may be a polygonal cylinder. The rear end portion of the inflatable member 28 is liquid-tightly fixed to the distal portion of the body portion 24 by adhesive bonding or thermal fusion. The tip portion of the inflatable member 28 is similarly liquid-tightly fixed to the distal portion of the guide portion 29.

The inflatable member 28 forms an inflation space between its inner surface and the outer surface of the body portion 24. The inflation space communicates with the lumen 26 through the perforation 30 of the body portion 24. The inflatable member 28 is preferably formed of a somewhat flexible material and for the material, for example thermoplastic resins including polyolefin such as polyethylene, polypropylene, and ethylene-propylene copolymer, polyvinyl chloride, polyester, ethylene-vinyl acetate copolymer, cross-linked ethylene-vinyl acetate copolymer, polyamide elastomer and polyurethane, silicone rubber and latex rubber can be used. The above thermoplastic resins are preferred and cross-linked ethylene-vinyl acetate copolymer is more preferred.

The front and the back parts of the inflatable member 28 between its cylindrical part and its fixed tip portion and rear end portion are tapered. The inflatable member 28 during its inflation preferably has an outer diameter of the cylindrical part of 1.20~35.00 mm, more preferably 1.50~30.00 mm, a length of the cylindrical part of 10.00~80.00 mm, more preferably 15.00~75.00 mm and a total length of 15.00~120.00 mm, more preferably 20.00~100.00 mm.

The hub is similarly shown in FIG. 10 fixed to a proximal end of the body portion 24. The hub has an opening communicating with the lumen 26 and constituting an injection post for injecting a fluid for expansion of inflatable member 28.

Figure 6:
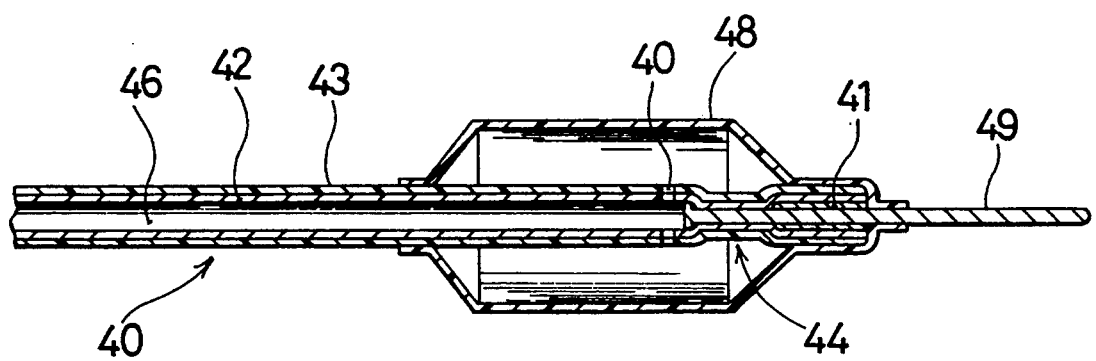
FIG. 6 is a partial longitudinal cross section of a catheter according to another preferred embodiment of the present invention.

Next, an embodiment wherein the catheter of the present invention is applied to a catheter for dilating a blood vessel shown in FIG. 6 will be described.

The catheter 40 comprises a body portion 44 which forms an internal lumen 46 and includes a super-elastic metallic tube having perforation 50 in its distal portion; a guide portion 49 for guiding the catheter which is attached to the distal tip of the body portion 44; and a deflatable or foldable and inflatable member 48 which has a tip portion attached to the distal portion of the body portion 44 and a rear end portion attached to the body portion 44 at a position apart from the perforation 50 toward the proximal end and communicates with the lumen 46 through the perforation 50; and a hub (not shown) fixed to the proximal end of the body portion 44.

The catheter 40 of this embodiment is different from the catheter 20 of the above embodiment shown in FIG. 5 in the position at which the tip portion of the inflatable member 48 is fixed and in the shape of the body portion 44. It is the same as the catheter shown in Fig.5 and mentioned above in all points other than the above points.

The body portion 44 of the catheter 40 has an almost equal thickness over its entire length and the distal portion of the body portion 44 is not tapered. The rear end portion of the inflatable member 48 is attached to the body portion 44 at a position apart from the perforation 50 toward the proximal end. The tip portion of the inflatable member 48 is attached to the distal portion of the body portion 44. The tip portion of the inflatable member 48 completely covers the distal portion of the body portion 44 and extends to the guide portion 49. This enables the distal tip of the body portion 44 to be prevented from being exposed and minimizes the damage to the inner wall of a blood vessel during insertion of the catheter into the blood vessel.

The hub is similarly shown in FIG. 10 fixed to a proximal end of the body portion 44. The hub has an opening communicating with the lumen 46 and constituting an injection port for injecting a fluid for expansion of inflatable member 48.

Next, an embodiment wherein the catheter of the present invention is applied to a catheter for dilating a blood vessel shown in FIG. 7 and FIG. 9 will be described.

Figure 9:
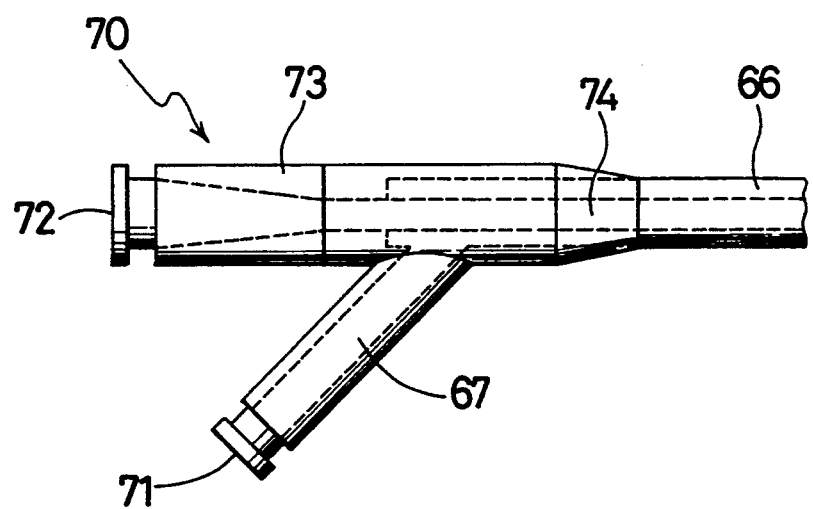
FIG. 9 is a view showing the proximal end of a catheter according to one preferred embodiment of the present invention.

The catheter 60 comprises an inner tube 61 having a body portion 64a, a proximal end portion 64b and a first lumen 66 whose tip is open; an outer tube 63 which is disposed coaxially with the inner tube 61, has a body portion 64a and a distal portion 64a, has a distal tip recessed by a predetermined distance from the distal tip of the inner tube 61 and forms a second lumen 67 between it and the outer surface of the inner tube 61; a deflatable or foldable and inflatable member 68 which has a tip portion attached to the inner tube 61 and a rear end portion attached to the outer tube 63 and communicates with the second lumen 67 near the rear end portion, a first opening 72 shown in FIG. 9 disposed at the proximal end portion of the inner tube and communicating with the first lumen 66; and a second opening 71 shown in FIG. 9 disposed at the proximal end portion of the outer tube 63 and, communicating with the second lumen 67. At least one of the inner tube 61 and the outer tube 63 includes a super-elastic metallic tube.

The catheter 60 consists of the inner tube 61, the outer tube 63, the inflatable member 68 and a branched hub 70.

The body portion 64a of the outer tube 63 has a super-elastic metallic tube 62. The outer tube 63 covers the outer surface of the super-elastic metallic tube 62 and protrudes from its distal end to form a distal portion 64b. The super-elastic metallic tube 62 may extend to the distal end of the outer tube 63. The super-elastic metallic tube 62 is preferably formed of a super-elastic alloys such as a Ti-Ni alloys containing 49~58 atom % of Ni, Cu-Zn alloys containing 38.5~41.5% by weight of Zn, Cu-Zn-X alloys containing 1~10% by weight of X wherein X is selected from the group consisting of Be, Si, Sn, Al and Ga, or Ni-Al alloys containing 36~38 atom % of Al. The most preferred alloys are Ti-Ni alloys of the above composition. The super-elastic metallic tube 62 preferably has an outer diameter of 0.6~2.0 mm, more preferably 0.8~1.6 mm and a wall thickness of 40~200 $\mu$m, more preferably 50~150 $\mu$m. It preferably has a length of 300~4,000 mm, more preferably 800~3,000 mm a buckling strength (yield stress under load) of 5~200 kg/mm$^2$ at 22° C., more preferably 8~150 kg/mm$^2$ at 22° C., and a restoring stress (yield stress upon unloading) of 3~180 kg/mm$^2$ at 22° C., more preferably 5~130 kg/mm$^2$ at 22° C. The outer tube 63 preferably has an outer diameter of 0.60~2.00 mm, more preferably 0.80~1.60 mm and an inner diameter of 0.50~1.90 mm preferably 0.60~1.40 mm. The difference between the outer diameter of the inner tube 61 and the inner diameter of the outer tube 63 preferably is 0.05~0.20 mm, more preferably 0.1~1.20 mm and the wall thickness of the outer tube 63 is 0.05~0.75 mm, more preferably 0.1~0.3 mm.

The outer tube 63 is preferably formed of a somewhat flexible material and for the material, for example, thermoplastic resins such as polyolefin (e.g.,polyethylene, polypropylene, ethylene-propylene copolymer), polyvinyl chloride, polyester, ethylene-vinyl acetate copolymer, polyamide elastomer and polyurethane and silicone rubber can be used. The above thermoplastic resins are preferred and polyolefins are more preferred.

The outer surface of the outer tube 63 may be coated with a biocompatible especially antithrombotic resin such as polyhydroxyethyl methacrylate or hydroxyethyl methacrylate-styrene copolymer (e.g., a HEMA-St-HEMA block copolymer).

The inner tube 61 is located inside the outer tube 63 and the distal portion of the inner tube 61 protrudes from the outer tube 63. The inner tube 62 preferably has an outer diameter of 0.40~1.60 mm, more preferably 0.50~1.30 mm and an inner diameter of 0.25~1.50 mm, more preferably 0.30~1.10 mm.

The inner tube 61 is preferably formed of a somewhat flexible material and for the material, for example, thermoplastic resins such as polyolefins (e.g., polyethylene, polypropylene, ethylene-propylene copolymer), polyvinyl chloride, polyester, ethylene-vinyl acetate copolymer, polyamide elastomer and polyurethane can be used. The above thermoplastic resins are preferred and polyolefins are more preferred.

The second lumen 67 is formed by the outer surface of the inner tube 61 and the inner surface of the outer tube 63. Therefore, the second lumen 67 has a sufficient volume. The tip of the second lumen 67 communicates with the internal space of the inflatable member 68 and the proximal end of the second lumen 67 communicates with the second opening 71 shown in FIG. 9 which forms an injection port for injecting a fluid (e.g., a contrast medium for angiography) for dilating the inflatable member 68. The second opening 71 is formed in the branched hub 70 shown in FIG. 9.

Figure 7:
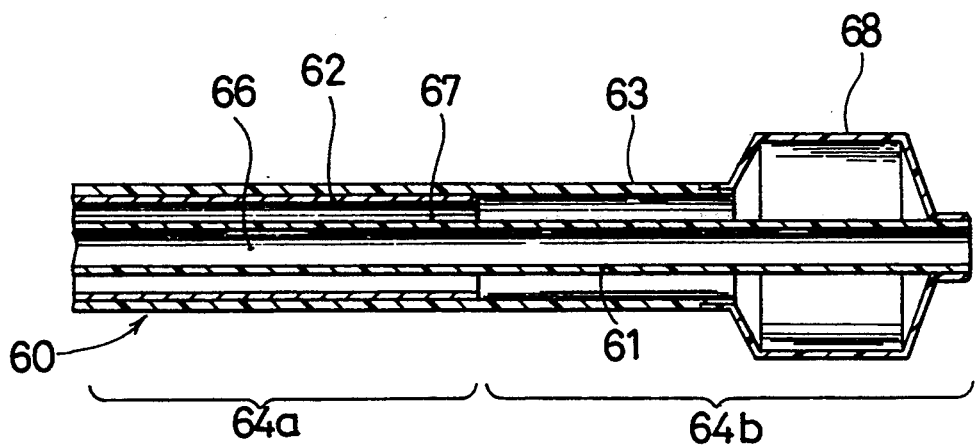
FIG. 7 is a partial longitudinal cross section of a catheter according to another preferred embodiment of the present invention.
Figure 8:
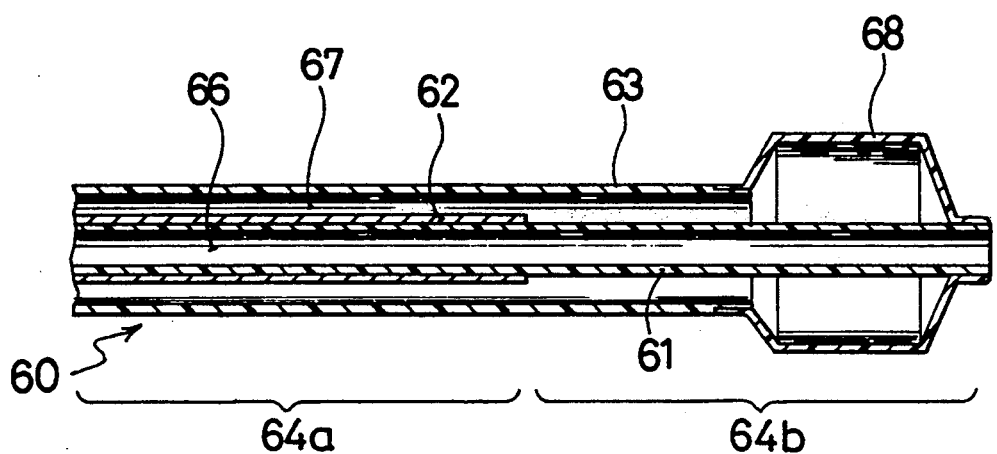
FIG. 8 is a partial longitudinal cross section of a catheter according to another preferred embodiment of the present invention.

A super-elastic metallic tube may not be disposed on the outer tube 63 as in the catheter shown in FIG. 7 and, as shown in FIG. 8, the inner tube 61 may be provided with the super-elastic metallic tube 62. In such a case, the super-elastic metallic tube 62 may be disposed on the outer surface of the inner tube.

The inflatable member 68 is deflatable or foldable and can be folded around the inner tube 61. At least a part of the inflatable member 68 is an almost circular cylinder having an almost equal diameter so that a stenosis portion in a blood vessel can easily be dilated and the inflatable member 68 is foldable. The above almost circular cylindrical part may not be a completely circular cylinder and may be a polygonal cylinder. The rear end portion of the inflatable member 68 is liquid-tightly fixed to the distal portion of the outer tube 63 by adhesive bonding or thermal fusion and the tip portion of the inflatable member 68 is similarly liquid-tightly fixed to the distal portion of the inner tube 61. The inflatable member 68 forms an inflatable space between its inner surface and the outer surface of the inner tube 61. The rear end portion of the expansion space communicates with the second lumen 67 over the entire circumference. Therefore, since the second lumen 67 has a relatively large volume, the fluid for inflation can easily be injected into the inflatable member 68 through the second lumen.

The inflatable member 68 is preferably formed of a somewhat flexible material and for the material, for example, thermoplastic resins such as polyolefins (e.g., polyethylene, polypropylene, ethylene-propylene copolymer, ethylene-vinyl acetate copolymer, cross-linked ethylene-vinyl acetate copolymer), polyvinyl chloride, polyester, polyamide elastomer and polyurethane, silicone rubber and latex rubber can be used. The above thermoplastic resins are preferred and cross-linked ethylene-vinyl acetate copolymer are more preferred. The inflatable member 68 during its inflation preferably has an outer diameter of the cylindrical part of 1.20~35.00 mm, more preferably 1.50~30.00 mm, a length of the cylindrical part of 10.00~80.00 mm, more preferably 15.00~75.00 mm and a total length of 15.00~120.00 mm, more preferably 20.00~100.00 mm.

Furthermore, in the catheter equipped with the inflatable member according to the present invention, it is preferred for facilitating the insertion into a blood vessel and further into a guide catheter to be mentioned later to apply hydrophilic treatment to areas having the possibility of contacting with blood during use, that is to say, the outer surface of the outer tube 63 and the outer surface of the inflatable member 68 so as to make them exhibit lubricity when contacted with blood or the like. Such hydrophilic treatments include coating with a hydrophilic polymer such as poly(2-hydroxyethyl methacrylate), polyhydroxyethyl acrylate, hydroxypropyl cellulose, methylvinyl ether-maleic anhydride copolymer, polyethylene glycol, polyacrylamide or polyvinyl pyrrolidone.

The branched hub 70 consists of an inner tube hub 73 which has the first opening 72 communicating with the first lumen 66 and constituting a guide wire port and is fixed to the inner tube 61 and an outer tube hub 74 which has the second opening 71 communicating with the second lumen and constituting an injection port for an inflating fluid and is fixed to the outer tube 63. The inner tube hub 73 and the outer tube hub 74 are fixed together.

The branched hub 70 is preferably formed of a thermoplastic resin such as polycarbonate, polyamide, polysulfone, polyallylate or methacrylate-butylene-styrene copolymer. Instead of providing such a branched hub 70, for example, a tube having a port member forming an opening at the proximal end may be liquid-tightly attached to each of the first and the second lumens.

Since the catheter of the present invention comprises a body portion, a leading edge and an internal lumen and at least the above body portion includes a super-elastic metallic tube, the catheter of the present invention has a high efficiency of transmitting the pushing force given at its proximal end (pushuability) and has a high torque transmission efficiency. Furthermore, since the body portion of the catheter includes a super-elastic metallic tube, the wall thickness of the body portion can be made sufficiently thin and a catheter with a smaller diameter can be formed.

Since the catheter of the present invention is a catheter equipped with an inflating member which comprises a body portion forming an internal lumen and including a super-elastic metallic tube having openings in its distal portion; a guide portion for guiding the catheter which is attached to the distal tip of said body portion; and a deflatable or foldable inflating member which has a tip portion attached to the above guide portion or the distal portion of the body portion and a rear end portion attached to the body portion and communicates with the lumen through the openings. The catheter of the present invention has a high efficiency of transmitting the pushing force given at its proximal end (pushability) and a high torque transmission efficiency. Furthermore, since the body portion of the catheter includes a super-elastic metallic tube, the wall thickness of the body portion can be made sufficiently thin and a catheter with a smaller diameter can be formed.

Since the catheter of the present invention comprises an inner tube having a body portion, a distal portion and a first lumen whose tip is open; an outer tube which is disposed coaxially with said inner tube, has a body portion, a distal portion and a distal tip recessed by a predetermined distance from the distal tip of the inner tube and forms a second lumen between it and the outer surface of said inner tube; a deflatable or foldable inflating member which has a tip portion attached to the inner tube and a rear end portion attached to the outer tube and communicates with the second lumen near said rear end portion; a first opening disposed at the proximal end portion of said inner tube and communicating with the above first lumen; and a second opening disposed at the proximal end portion of the above outer tube and communicating with the second lumen and at least one of the body portions of the inner and outer tubes includes a super-elastic metallic tube. The catheter has a high efficiency of transmitting the pushing force given at its proximal end (pushability) and a high torque transmission efficiency. Furthermore, since the body portion of the catheter includes a super-elastic metallic tube, the wall thickness of the body portion can be made sufficiently thin and a catheter with a small diameter can be formed.

We claim:

1. A catheter comprising:
    an inner tube having a body portion, a distal portion and a first lumen having an open digital tip;
    an outer tube which is disposed coaxially with said inner tube, said outer tube having a body portion, a distal portion, and a distal tip recessed by a predetermined distance from the distal tip of said inner tube, and forming a second lumen between an inner surface of said outer tube and an outer surface of said inner tube;
    a contractible and inflatable member which has a tip portion attached to said inner tube and a rear end portion attached to said outer tube, and which communicates with said second lumen near said rear end portion;
    a first opening disposed at a proximal portion of said inner tube and communicating with said first lumen; and
    a second opening disposed at a proximal portion of said outer tube and communicating with said second lumen;
    and wherein:
    said outer tube comprises a super-elastic alloy tube, and a flexible synthetic resin tube covering an outer surface of said super-elastic alloy tube; said flexible synthetic resin tube of said outer tube protrudes distally from a distal end portion of said super-elastic alloy tube to form said distal portion of said outer tube;
    said inner tube is made of flexible synthetic resin; and
    said contractible and inflatable member is made of flexible synthetic resin, said tip portion of said contractible and inflatable member is attached to said flexible synthetic resin inner tube, and said rear end portion of said contractible and inflatable member is attached to said distal portion of said flexible synthetic resin tube of said outer tube.

2. The catheter of claim 1, wherein said contractible and inflatable member is deflatable to take a contracted state.

3. The catheter of claim 1, wherein said contractible and inflatable member is foldable to take a contracted state.

4. A catheter of claim 1, wherein an outer surface of said outer tube and an outer surface of said contractible and inflatable member comprise a hydrophilic treatment thereon so that said treated outer surfaces have lubricity.

5. The catheter of claim 1, wherein said flexible synthetic resin is selected from the group consisting of polyethylene elastomer, polypropylene elastomer, ethylene-propylene copolymer elastomer, polyvinyl chloride, ethylene-vinyl acetate copolymer, polyamide elastomer, polyurethane, fluorine resin, and silicone rubber.

6. The catheter of claim 1, wherein said super-elastic alloy is selected from the group consisting of Ti-ni alloys containing 49 to 58 atom % of Ni, Cu-Zu alloys containing 38.5 to 41.5% by weight of Zn, Ni-Al alloys containing 36 to 38 atom % of Al, and Cu-Zn-X alloys containing 1 to 10% by weight of X wherein X is selected from the group consisting of Be, Si, Sn, Al and Ga.

7. The catheter of claim 5, wherein said super-elastic alloy is selected from the group consisting of Ti-ni alloys containing 49 to 58 atom % of Ni, Cu-Zu alloys containing 38.5 to 41.5% by weight of Zn, Ni-Al alloys containing 36 to 38 atom % of Al, and Cu-Zn-X alloys containing 1 to 10% by weight of X wherein X is selected from the group consisting of Be, Si, Sn, Al and Ga.

8. The catheter of claim 7, wherein:
    said flexible synthetic resin is selected from the group consisting of polyamide elastomer and polyurethane; and
    said super-elastic alloy is a Ti-Ni alloy containing 49 to 58 atom % of Ni.

9. The catheter of claim 8 wherein:
    an outer surface of said outer tube and an outer surface of said contractible and inflatable member comprise a hydrophilic treatment thereon so that said treated outer surfaces have lubricity; and
    said hydrophilic treatment thereon is a coating of a hydrophilic polymer selected from the group consisting of poly(2-hydroxyethyl methacrylate), polyhydroxyethyl acrylate, hydroxypropyl cellulose, methylvinyl ether-maleic anhydride copolymer, polyethylene glycol, polyacrylamide, and polyvinyl pyrrolidone.

10. The catheter of claim 1, wherein said super-elastic alloy tube has an outer diameter of from about 0.6 to 2 mm, and a wall thickness of about 40 to 200 $\mu$m.

11. The catheter of claim 10, wherein said super-elastic alloy tube has an outer diameter of from about 0.8 to 1.6 mm and a wall thickness of about 50 to 150 μm.

12. The catheter of claim 10, wherein said inner tube has an outer diameter of about 0.4 to 1.6 mm.

13. A catheter comprising:
an inner tube having a body portion, a distal portion and a first lumen having an open distal tip;
an outer tube which is disposed coaxially with said inner tube, said outer tube having a body portion, a distal portion and a distal tip recessed by predetermined distance from the distal tip of said inner tube, and forming a second lumen between an inner surface of said outer tube and an outer surface of said inner tube;
a contractible and inflatable member which has a tip portion attached to said inner tube and a rear end portion attached to said outer tube, and which communicates with said second lumen near said rear end portion;
a first opening disposed at a proximal portion of said inner tube and communicating with said first lumen; and
a second opening disposed at a proximal portion of said outer tube and communicating with said second lumen; and wherein:
said inner tube comprises a super-elastic alloy tube, and a flexible synthetic resin tube fused to an inner surface of said super-elastic alloy tube;
said flexible synthetic resin tube of said inner tube protrudes distally from a distal end portion of said super-elastic alloy tube to form said distal portion of said inner tube;
said outer tube is made of flexible synthetic resin; and
said contractible and inflatable member is made of flexible synthetic resin, said tip portion of said contractible and inflatable member is attached to said flexible synthetic resin tube of said inner tube, and said rear end portion of said contractible and inflatable member is attached to said distal portion of said flexible synthetic resin outer tube.

14. The catheter of claim 13, wherein said contractible and inflatable member is deflatable to take a contracted state.

15. The catheter of claim 13, wherein said contractible and inflatable member is foldable to take a contracted state.

16. A catheter of claim 13, wherein an outer surface of said outer tube and an outer surface of said contractible and inflatable member comprise a hydrophilic treatment thereon so that said treated outer surfaces have lubricity.

17. The catheter of claim 13, wherein said flexible synthetic resin is selected from the group consisting of polyethylene elastomer, polypropylene elastomer, ethylene-propylene copolymer elastomer, polyvinyl chloride, ethylene-vinyl acetate copolymer, polyamide elastomer, polyurethane, fluorine resin, and silicone rubber.

18. The catheter of claim 13, wherein said super-elastic alloy is selected from the group consisting of Ti-ni alloys containing 49 to 58 atom % of Ni, Cu-Zu alloys containing 38.5 to 41.5% by weight of Zn, Ni-Al alloys containing 36 to 38 atom % of Al, and Cu-Zn-X alloys containing 1 to 10% by weight of X wherein X is selected from the group consisting of Be, Si, Sn, Al and Ga.

19. The catheter of claim 17, wherein said super-elastic alloy is selected from the group consisting of Ti-ni alloys containing 49 to 58 atom % of Ni, Cu-Zu alloys containing 38.5 to 41.5% by weight of Zn, Ni-Al alloys containing 36 to 38 atom % of Al, and Cu-Zn-X alloys containing 1 to 10% by weight of X wherein X is selected from the group consisting of Be, Si, Sn, Al and Ga.

20. The catheter of claim 19, wherein:
said flexible synthetic resin is selected from the group consisting of polyamide elastomer and polyurethane; and
said super-elastic alloy is a Ti-Ni alloy containing 49 to 58 atom % of Ni.

21. The catheter of claim 20 wherein:
an outer surface of said outer tube and an outer surface of said contractible and inflatable member comprise a hydrophilic treatment thereon so that said treated outer surfaces have lubricity; and
said hydrophilic treatment thereon is a coating of a hydrophilic polymer selected from the group consisting of poly(2-hydroxyethyl methacrylate), polyhydroxyethyl acrylate, hydroxypropyl cellulose, methylvinyl ether-maleic anhydride copolymer, polyethylene glycol, polyacrylamide, and polyvinyl pyrrolidone.

* * * * *

UNITED STATES PATENT AND TRADEMARK OFFICE
CERTIFICATE OF CORRECTION

PATENT NO. : 5,397,306
DATED : March 14, 1995
INVENTOR(S) : NOBUYOSHI et al

It is certified that error appears in the above-indentified patent and that said Letters Patent is hereby corrected as shown below:

In the Title Page, under Section [56] References Cited, after "5,279,560  1/1994  Morrill et al....604/96"

insert  -- FOREIGN PATENT DOCUMENTS

```
    58-32738   2/83    Japan
   0,279,959   8/88    EPA
WO 89/08473   9/79    WIPO
```

OTHER PUBLICATIONS

Publication "SHAPE MEMORY AND SUPER-ELASTICITY EFFECTS IN NiTi ALLOYS" and English translation, Vol. 30, No. 4, pages 185-192.--

Column 3, line 41,

Change "2220C" to --22°C--

UNITED STATES PATENT AND TRADEMARK OFFICE
CERTIFICATE OF CORRECTION

PATENT NO. : 5,397,306
DATED : March 14, 1995
INVENTOR(S) : NOBUYOSHI et al.

It is certified that error appears in the above-indentified patent and that said Letters Patent is hereby corrected as shown below:

Column 7, line 23,
Change "perforation" to --perforations--.

Signed and Sealed this

Fourteenth Day of May, 1996

Attest:

BRUCE LEHMAN

Attesting Officer      Commissioner of Patents and Trademarks